(12) United States Patent
Medford et al.

(10) Patent No.: US 10,143,841 B2
(45) Date of Patent: Dec. 4, 2018

(54) TRANSCRANIAL NEUROSTIMULATION SYSTEM FOR A VEHICLE

(71) Applicant: Ford Global Technologies, LLC, Dearborn, MI (US)

(72) Inventors: Nathan Medford, London (GB); Eunhee Jo, London (GB); Liberty Fearns, London (GB); Ben Carroll, London (GB); Marcus Hoggarth, Herfordshire (GB)

(73) Assignee: Ford Global Technologies, LLC, Dearborn, MI (US)

( * ) Notice: Subject to any disclaimer, the term of this patent is extended or adjusted under 35 U.S.C. 154(b) by 0 days.

(21) Appl. No.: 15/454,111

(22) Filed: Mar. 9, 2017

(65) Prior Publication Data

US 2017/0259059 A1    Sep. 14, 2017

(30) Foreign Application Priority Data

Mar. 10, 2016 (GB) .................................. 1604151.9

(51) Int. Cl.
| | |
|---|---|
| *A61N 1/36* | (2006.01) |
| *A61B 5/0476* | (2006.01) |
| *A61B 5/00* | (2006.01) |
| *A61N 1/04* | (2006.01) |
| *A61B 5/0205* | (2006.01) |
| *B60N 2/80* | (2018.01) |
| *A61B 5/021* | (2006.01) |
| *A61B 5/024* | (2006.01) |
| *A61B 5/08* | (2006.01) |

(52) U.S. Cl.
CPC ...... *A61N 1/36025* (2013.01); *A61B 5/02055* (2013.01); *A61B 5/4836* (2013.01); *A61B 5/6893* (2013.01); *A61N 1/0456* (2013.01); *A61N 1/0472* (2013.01); *A61N 1/36031* (2017.08); *B60N 2/80* (2018.02); *A61B 5/021* (2013.01); *A61B 5/024* (2013.01); *A61B 5/0476* (2013.01); *A61B 5/0816* (2013.01); *A61N 1/0476* (2013.01); *B60N 2002/899* (2018.02)

(58) Field of Classification Search
CPC .............. A61N 1/36025; A61N 1/0456; A61N 1/0476; A61B 5/6893
See application file for complete search history.

(56) References Cited

U.S. PATENT DOCUMENTS

| | | | |
|---|---|---|---|
| 2003/0195588 A1 | 10/2003 | Fischell et al. | |
| 2005/0061569 A1* | 3/2005 | Pascolo .............. | A61N 1/36014 180/271 |
| 2006/0206163 A1* | 9/2006 | Wahlstrand ........ | A61N 1/36071 607/46 |
| 2007/0173908 A1 | 7/2007 | Begnaud | |
| 2007/0179579 A1* | 8/2007 | Feler .................. | A61N 1/36071 607/117 |
| 2012/0197353 A1* | 8/2012 | Donnelly ............. | A61B 5/6805 607/62 |

(Continued)

FOREIGN PATENT DOCUMENTS

WO    2009132372 A2    11/2009

*Primary Examiner* — William J Levicky
(74) *Attorney, Agent, or Firm* — Vichit Chea; Price Heneveld LLP

(57) ABSTRACT

A transcranial neurostimulation system for a vehicle, the transcranial neurostimulation system comprising at least one electrode formed into an article of vehicle furniture such as a headrest of a seat.

19 Claims, 3 Drawing Sheets

(56) References Cited

U.S. PATENT DOCUMENTS

| | | | |
|---|---|---|---|
| 2013/0009761 A1* | 1/2013 | Horseman | A61B 5/6893 340/425.5 |
| 2013/0090704 A1 | 4/2013 | Kolen et al. | |
| 2015/0105641 A1* | 4/2015 | Austin | A61B 5/6891 600/364 |

* cited by examiner

TRANSCRANIAL NEUROSTIMULATION SYSTEM FOR A VEHICLE

FIELD OF THE INVENTION

This disclosure generally relates to a transcranial neurostimulation system for a vehicle, and in particular, but not exclusively, relates to a transcranial neurostimulation system forming at least a portion of a headrest of a vehicle seat.

BACKGROUND OF THE INVENTION

It is common for an individual to experience motion sickness (kinetosis) when travelling in a vehicle. Motion sickness may be caused by conflict between the vestibular, visual and motor inputs sent to the brain. For example, when the vehicle is in motion and the individual is reading a book, the inner ear detects that the individual is moving but the eyes do not, which creates a conflict in the brain and can cause the individual to experience motion sickness.

Behavioral and environmental factors play a key part in causing motion sickness. For example driving style, visibility from within the vehicle and the ability to determine the direction of motion may have an effect on an individual's likelihood to experience motion sickness.

Motion sickness can affect anyone, and research has shown that there is a genetic pattern within those who are most susceptible. Women are believed to be at greater risk of suffering motion sickness compared to men, with 27.3% of women and 18.6% of men being believed to suffer from motion sickness.

When an individual is traveling in a vehicle, the type of activity undertaken by the individual may influence the signals which are sent to the brain. For example, where an individual is concentrating on their surroundings, i.e. an environment external to the vehicle, motion sickness may be less likely to occur. However, with the advent of semi- or fully autonomous vehicles, an individual travelling in a vehicle is more likely to engage in activities, such as reading, writing and/or watching visual entertainment, which can direct the concentration away from the environment external to the vehicle, and increase the risk of that individual experiencing motion sickness.

It is known to use behavioral and/or pharmacologic therapy, such as acupressure therapy and transdermal patch therapy, to alleviate the symptoms of motion sickness. However, such therapies need to be actioned by an individual and may have side effects, for example where drugs are taken.

SUMMARY OF THE INVENTION

According to one aspect of the present invention, a transcranial neurostimulation system for a vehicle is provided. The transcranial neurostimulation system including at least one electrode formed into a headrest of a vehicle seat, wherein the at least one electrode comprises a conductive thread stitched and/or woven into the material of a covering of the headrest.

The transcranial neurostimulation system may comprise a controller configured to adjust the operation of the transcranial neurostimulation system. The controller may be configured to adjust the operation of the transcranial neurostimulation system depending on the condition of an occupant of the vehicle. For example, the controller may be configured to adjust the operation of the transcranial neurostimulation system depending on one or more vital signs of an occupant of the article of vehicle furniture such as a vehicle seat.

The controller may be configured to adjust the operation of the transcranial neurostimulation system depending on the operational state of the vehicle. For example, the controller may be configured to adjust the operation of the transcranial neurostimulation system depending on the speed, direction, acceleration and/or any other appropriate operational parameter of the vehicle.

The transcranial neurostimulation system may comprise at least one first sensor, for example an occupant sensor, configured to determine a condition of an occupant of the vehicle. The first sensor may be configured to determine the direction in which the occupant is looking. The first sensor may be configured to determine the heart rate of the occupant. The first sensor may be configured to determine the blood pressure of the occupant. The first sensor may be configured to determine the temperature of the occupant. The first sensor may be configured to determine the brain activity of the occupant. The first sensor may be configured to determine the respiration rate of the occupant. The first sensor may be configured to determine the vocal activity of the occupant, for example one or more words, phrases and/or sounds made by the occupant.

The first sensor may be integral to the article of vehicle furniture. The first sensor may be a sensor of the vehicle, for example an existing sensor configured to capture data regarding the occupant of the vehicle. The existing occupant sensor may be any appropriate sensor configured to determine the condition of an occupant of the vehicle for a purpose other than controlling the operation of the transcranial neurostimulation system. The controller may be configured to repurpose the use of the existing occupant sensor.

The transcranial neurostimulation system may comprise at least one second sensor, for example a vehicle sensor, configured to determine the operational state of the vehicle. The second sensor may be configured to determine the speed, direction, acceleration and/or any other appropriate operational parameter of the vehicle. The second sensor may be integral to the article of vehicle furniture or the vehicle. The second sensor may be a sensor of the vehicle, for example an existing sensor configured to capture data regarding the operational state of the vehicle. The existing vehicle sensor may be any appropriate sensor configured to determine the operational state of the vehicle for a purpose other than controlling the operation of the transcranial neurostimulation system. The controller may be configured to repurpose the use of the existing vehicle sensor.

The transcranial neurostimulation system may comprise one or more actuators configured to position the electrodes. For example, the transcranial neurostimulation system may comprise one or more actuators configured to move the electrodes relative to a region of the occupant's head. The actuator may be an adaptive support element configured to support a part of the body of a user of the vehicle.

The electrodes may be provided at least partially within a headrest of the article of vehicle furniture or seat. The electrodes may be provided in the material of a cover of a headrest for use in the vehicle. The headrest may be integral to the article of vehicle furniture. The headrest may be movably securable to the article of vehicle furniture. The electrodes may be provided in the material of a cover of a pillow, which may be configured for specific use in the vehicle.

The transcranial neuro stimulation system may be activated by way of contact between a portion of the article of vehicle furniture and the head of an occupant of the vehicle furniture. The transcranial neurostimulation system may comprise an anode electrode. The transcranial neurostimulation system may comprise a cathode electrode. The transcranial neurostimulation system may be activated by way of completing an electric circuit between at least a portion of the anode electrode and at least a portion of the cathode electrode. The anode electrode may be used to locate a particular region of the occupant's head. The cathode electrode may act as ground for the transcranial neurostimulation system. The transcranial neurostimulation system may be configured to operate using a low voltage supply, for example approximately a 9 volt supply.

According to one embodiment, there is provided a material having at least one electrode of a transcranial neurostimulation device woven and/or stitched into the material. The electrode may be a conductive thread that may be stitched into the material of a covering of the headrest or woven into the material of a covering of the headrest or may both be stitched and woven into the material of a covering of the headrest or other vehicle furniture. There may be a pair of electrodes formed into the headrest.

According to another embodiment, a vehicle transcranial neurostimulation system includes at least one electrode formed into a headrest of vehicle furniture. At least one electrode includes a conductive thread stitched and/or woven into the material of a covering of the headrest.

According to a further embodiment, a vehicle seat is provided. The vehicle seat includes a headrest including a material forming a covering, and a transcranial neurostimulation system including at least one electrode formed into the headrest. The at least one electrode comprises a conductive thread stitched and/or woven in the material.

In the context of the present disclosure, the term "transcranial neurostimulation device" is understood to include any device that is configured to provide transcranial neurostimulation by virtue of at least one of transcranial direct current stimulation (tDCS), transcranial alternating current stimulation (tACS), transcranial random noise stimulation (tRNS), transcranial magnetic stimulation (tMS), or any other appropriate type of transcranial electric and/or magnetic stimulation.

In the context of the present disclosure, the term "vehicle furniture" is understood to mean any appropriate furniture that can be used to make the interior and/or exterior of the vehicle suitable for being occupied/used by one or more individuals. The vehicle furniture may, for example, be a seat, a bench, a headrest, an armrest, a footrest, a table, and/or a desk. The vehicle furniture may be configured to support a cranial region of an occupant when the occupant is using the article of vehicle furniture.

To avoid unnecessary duplication of effort and repetition of text in the specification, certain features are described in relation to only one or several aspects or arrangements of the disclosure. However, it is to be understood that, where it is technically possible, features described in relation to any aspect or arrangement of the disclosure may also be used with any other aspect or arrangement of the disclosure.

These and other aspects, objects, and features of the present invention will be understood and appreciated by those skilled in the art upon studying the following specification, claims, and appended drawings.

DETAILED DESCRIPTION OF THE PREFERRED EMBODIMENTS

The condition of the kinetosis, or motion sickness as it is more commonly known, is experienced when there is a disparity between visually perceived movement and the movement sensed by the vestibular system of an occupant of a vehicle. Common symptoms of kinetosis include dizziness, nausea and fatigue, each of which can make a journey in the vehicle unpleasant for the occupant.

In order to increase the comfort of the occupant of the vehicle during a journey, it is desirable to reduce the ill effects of kinetosis. It is known to use behavioral and/or pharmacologic therapy, such as acupressure therapy and transdermal patch therapy, to alleviate the symptoms of motion sickness. However, such therapies need to be actioned by the occupant and may have side effects on the occupant, for example where drugs are taken.

Research into transcranial direct current neurostimulation (tDCS) has shown that electrical stimulation of particular areas of the brain can alleviate the symptoms of motion sickness. tDCS therapy involves placing two electrodes, an anode and a cathode, in contact with the occupant's head, and passing a small current between the electrodes. In this manner, the flow of current between the electrodes can affect the neuronal excitability of a specific area of the brain being stimulated by the tDCS therapy. This change of the neuronal excitability can lead to an alteration of the function of the brain, and in particular can alter the function of the region of the brain that is associated with motion sickness.

Figure 1:
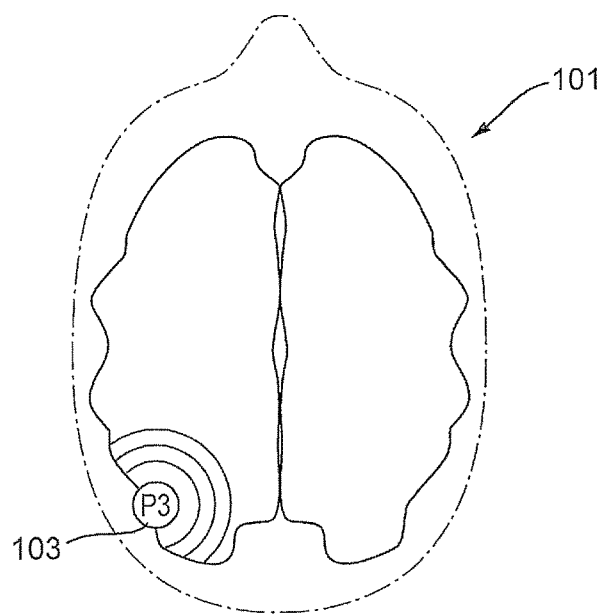
FIG. 1 is a top schematic view of a human head showing the region of the brain.

FIG. 1 shows a schematic of a human head 101, and in particular shows a region of the brain 103 where the P300 (P3) wave is a component of an event related potential. The P3 region 103 of the brain is located towards the rear of the left-hand side of the head 101, and the event related potential of the P3 region 103 may be associated with the symptoms of motion sickness.

Figure 2:
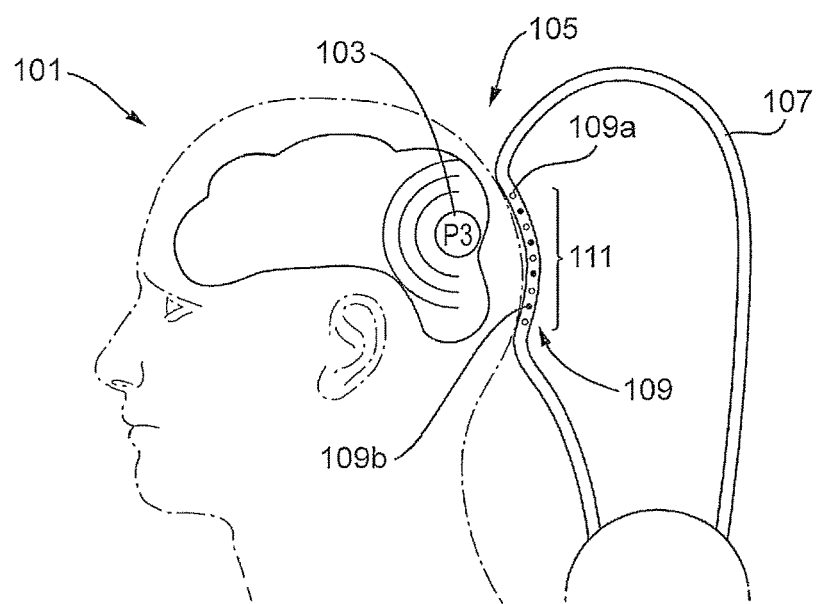
FIG. 2 is a side view of the head positioned against a headrest having a transcranial neurostimulation system, according to one embodiment.

FIG. 2 shows a transcranial neurostimulation system 105 according to one embodiment of the present disclosure. The transcranial neurostimulation system 105 comprises a plurality of electrodes 109 that are configured to apply an electric current between two points of the occupant's head 101. In the arrangement shown in FIG. 2, the electrodes 109 are formed into a headrest 107 of a vehicle seat. However, in one or more alternative arrangements, the electrodes 109 may be formed into any appropriate article of vehicle furniture. For example, the vehicle furniture may be a bed and the electrodes may be formed into a region of the bed against which the occupant can position their head 101. Additionally or alternatively, the electrodes may be formed into an article of vehicle furniture separate from, for example removable from, the vehicle, such as a pillow, cushion or headrest cover. It is understood, therefore, that the present disclosure provides an article, whether integral to or separate from a vehicle, that may be used to alleviate the symptoms of motion sickness.

As shown in the arrangement of FIG. 2, the electrodes 109 are integrated into a region 111 of the headrest 107 against which the occupant can position their head 101 when seated in the vehicle seat. Where the headrest 107 is covered in a fabric, each of the electrodes 109 may comprise one or more conductive threads, which may be stitched or woven into the material of the headrest 107. Where the headrest 107 is fabricated from a non-woven material, such as leather, the conductive threads can be stitched into the non-woven material such that at least a portion of each of the electrodes 109 protrudes from the surface of the non-woven material. However, the electrodes 109 may be integrated into the headrest 107 in any manner depending on the material from which the headrest 107 is fabricated. For example, where the headrest 107 is a molded plastic headrest, the electrodes 109 may be over-molded into a body portion of the headrest 107. Additionally or alternatively, the electrodes may be formed into a separate portion of material, which can be subsequently attached to a portion of the headrest 107, for example by virtue of stitching and/or gluing. In one arrangement, the electrodes 109 may be formed into a headrest cover configured to be attached to an existing headrest 107 of a vehicle.

Figure 3:
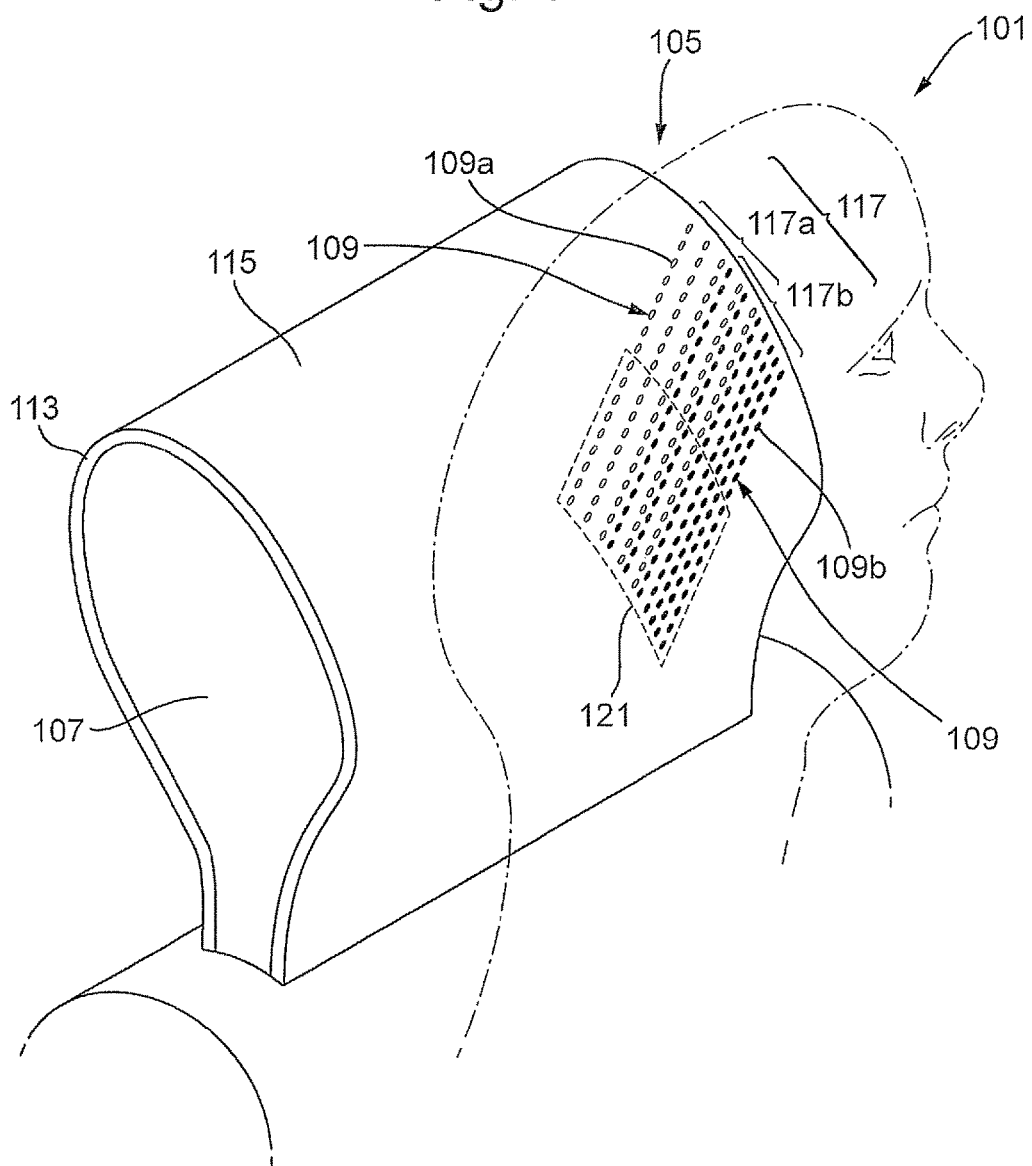
FIG. 3 is a rear perspective view of the head and the headrest having the transcranial neurostimulation system.

FIGS. 2 and 3 show arrangements where the transcranial neurostimulation system 105 is integrated into the headrest 107, such that the electrodes 109 are proximate to the occupant's head 101 when the occupant is seated in the vehicle seat. The transcranial neurostimulation system 105 is configured such that contact of the occupant's head 101 against the headrest 107 completes an electric circuit between at least two of the electrodes 109, for example between at least one anode 109a and at least one cathode 109b. The transcranial neurostimulation system 105 does not, therefore, require any input from the occupant of the vehicle in order to activate the transcranial neurostimulation system 105, since the occupant's head 101 is typically positioned near to and/or in contact with the headrest 107. As such, activation of the transcranial neurostimulation system 105 is by virtue of an action that occurs habitually whilst the occupant is seated in the vehicle seat, i.e. by virtue of the occupant using the headrest 107. In this manner, the occupant may not even realize that they have activated the transcranial neurostimulation system 105. Furthermore, the operation of the transcranial neurostimulation system 105 may be imperceptible to the occupant whilst the treatment is active, as there are no known side-effects of tDCS therapy. A further benefit is that tDCS therapy can be used to improve cognitive function in certain cases, which may in fact increase the concentration of a driver of the vehicle, for example on a long journey and/or in poor driving conditions.

The transcranial neurostimulation system 105 may be configured to activate when the occupant's head 101 engages the electrodes 109 and completes the electric circuit between the electrodes 109, such as between anode 109a and cathode 109b. In this manner, the transcranial neurostimulation system 105 may be configured to be active when the occupant's head 101 is in contact with the electrodes 109 and not active when the occupant's head 101 is remote from the headrest 107. In one arrangement, there may be no other type of control over the operation of the transcranial neurostimulation system 105, and operation of the transcranial neurostimulation therapy can be unnoticeable to the occupant of the vehicle.

Figure 4:
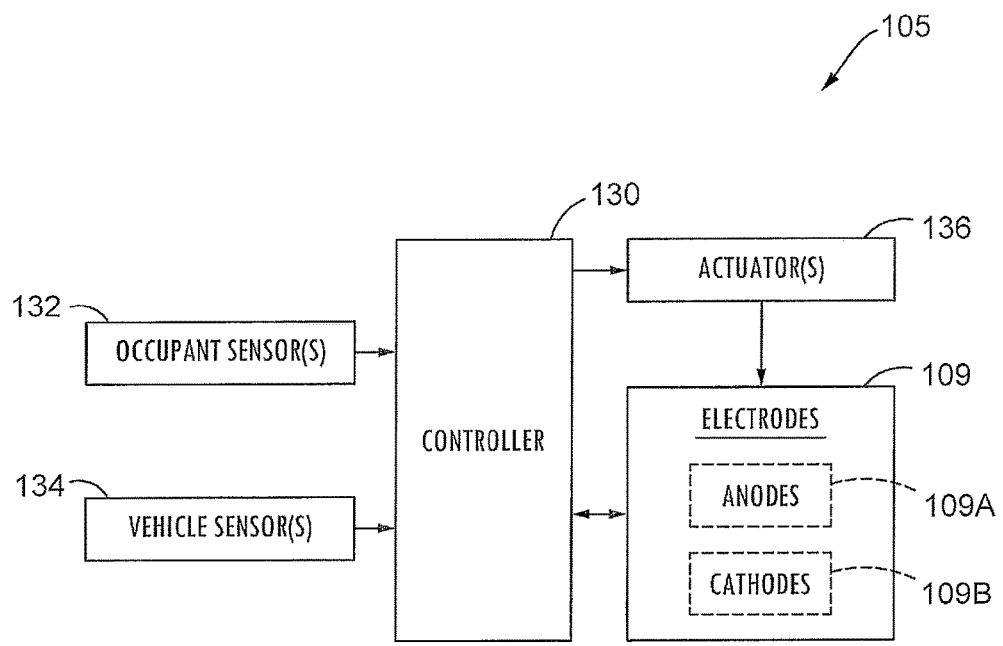
FIG. 4 is a block diagram further illustrating the transcranial neurostimulation system, according to one embodiment.

The transcranial neurostimulation system 105 may comprise a controller 130 as shown in FIG. 4 configured to adjust the operation of the transcranial neurostimulation system 105, for example depending on the condition of the occupant of the vehicle and/or the operational state of the vehicle. In one arrangement, the transcranial neurostimulation system 105 may be configured to determine when the occupant of the vehicle might experience motion sickness. The transcranial neurostimulation system 105 may comprise at least one occupant sensor 132 configured to determine a condition of the occupant of the vehicle. The occupant sensor 132 may be configured to determine one or more vital signs of the occupant, for example body temperature, blood pressure, pulse (heart rate), breathing rate (respiratory rate), and/or any other appropriate vital sign.

The controller 130 may be configured to adjust the operation of the transcranial neurostimulation system 105, for example by activating, deactivating and/or changing an operational level of the transcranial neurostimulation system 105. In one arrangement, the controller 130 may be configured to activate the transcranial neurostimulation system 105 when it is determined that one of more of the occupant's vital signs indicates that the occupant might be experiencing motion sickness. The controller 130 may be configured to increase or decrease the operational level of the transcranial neurostimulation system 105 depending on a determined change in the condition of the occupant.

Additionally or alternatively, the occupant sensor 132 may be configured to determine the direction in which the occupant is looking. For example, the occupant sensor 132 may comprise a camera configured to determine that the occupant is not looking through a window of the vehicle, and instead is reading or watching a display within the vehicle, or has their eyes closed. The controller 130 may be configured to activate the transcranial neurostimulation system 105 when it is determined that the occupant is not looking at the environment external to the vehicle. This may be advantageous as the transcranial neurostimulation system 105 can be configured to operate when there is a disparity between the vestibular and visual inputs that are sent to the occupant's brain.

Additionally or alternatively, the occupant sensor 132 may be configured to determine the level of movement of the occupant, for example by determining a change in the pressure distribution across the article of vehicle furniture that the occupant is using. The occupant sensor 132 may be configured to determine when the occupant is still for a period of time, which may indicate that the occupant is asleep. The occupant sensor 132 may be configured to determine if the occupant is agitated and is unable to remain still, which may indicate that the occupant is not feeling well. The controller 130 may be configured to activate the transcranial neurostimulation system 105 when it is determined that the occupant's movement corresponds to a pattern of movement that indicates that the occupant is likely to be suffering from motion sickness.

Additionally or alternatively, the occupant sensor 132 may be configured to determine the brain activity of the occupant. For example, the occupant sensor 132 may comprise one or more sensors configured to measure the electrical activity of one or more regions of the brain. In particular, the occupant sensor 132 may be configured to determine the activity of the P3 region 103 of the occupant's brain. The data collected from the occupant sensor may be used to map behavioral patterns of the occupant of the vehicle, which can be used to indicate when the occupant is likely to experience motion sickness. The controller 130 may be configured to activate the transcranial neurostimulation system 105 when the electrical activity of the brain is indicative that the occupant is experiencing motion sickness. In one arrangement, the electrodes 109 may be configured to measure the occupant's brain activity when the occupant's head is near to or against the headrest 107.

Additionally or alternatively, the occupant sensor 132 may be configured to determine the vocal activity of the occupant. For example, the occupant sensor 132 may comprise one or more microphones configured to record the speech of the occupant. In particular, the occupant sensor 132 may be configured to determine if the occupant says one or more predetermined phases that may indicate that the occupant is not feeling well. For example, the controller 130 may be configured to activate the transcranial neurostimulation system 105 when the occupant communicates to another occupant that they are not feeling well.

In other words, the controller 130 may be configured to record the behavior of the occupant and map one or more physical characteristics of the occupant, for example during a variety of driving conditions. In this manner, the controller 130 may be configured to activate the transcranial neurostimulation system 105 when the physical characteristics of the occupant correspond to a set of physical characteristics that indicate that the occupant is experiencing motion sickness.

The transcranial neurostimulation system 105 may comprise at least one vehicle sensor 134 configured to determine the operational state of the vehicle. For example, the vehicle sensor 134 may comprise an accelerometer configured to determine the motion of the vehicle, such as the manner in which the vehicle is being driven and/or the severity of movement of the vehicle. The controller 130 may be configured to determine the change in the acceleration of the vehicle, for example over a predetermined time period. In this manner, the transcranial neurostimulation system 105 may be configured to determine a rate of change of the direction in which the vehicle is travelling. Where the acceleration, or the rate of change of direction, is greater than a predetermined threshold, the controller 130 may be configured to activate the transcranial neurostimulation system 105. The predetermined threshold may be an acceleration and/or directional threshold beyond which the occupant is likely to experience motion sickness.

In one arrangement, the transcranial neurostimulation system 105 may be a stand-alone system that can be fitted to an article of vehicle furniture, such as the vehicle seat headrest. Where the transcranial neurostimulation system 105 is a stand-alone system, it may comprise one or more of the above mentioned occupant sensors 132 and/or one or more of the above mentioned vehicle sensors 134. The transcranial neurostimulation system 105 may be suitable to be installed across a wide range of vehicles, the sensors of the transcranial neurostimulation system 105 being able to determine the condition of the occupant and/or the vehicle without any interface to a vehicular system, according to one embodiment.

Additionally or alternatively, the transcranial neurostimulation system 105 may be configured to connect operatively with one or more vehicular systems. For example, the transcranial neurostimulation system 105 may be configured to connect operatively to one or more existing sensors of the vehicle. In this manner, the transcranial neurostimulation system 105 is able to utilize the data captured from a system of the vehicle, for example data regarding the condition of the occupant of the vehicle and/or data regarding the operative state of the vehicle.

The article of vehicle furniture may be any appropriate type of furniture, for example the headrest 107 or a cushion/pillow. For example, where the article of furniture is the headrest 107, the headrest may be a replacement headrest for a vehicle, i.e. a headrest produced by a non-original equipment manufacturer.

In one arrangement, the transcranial neurostimulation system 105 may comprise one or more actuators 136 configured to position the electrodes 109 relative to the head 101 of the occupant. For example, the electrodes 109 may be coupled to one or more mechanisms configured to move a portion of the headrest 107 closer to the region of the occupant's head 101 that corresponds to the P3 region 103 of the brain. The headrest 107 may comprise one or more adaptive support elements, for example, an active material configured to change shape upon excitation by electrical and/or thermal energy. In this manner, the transcranial neurostimulation system 105 may be configured to adapt to the shape of each individual occupant so that the electrode 109 is positioned for optimal effect.

The present disclosure is advantageous as it provides a system and method for preventing motion sickness, for example by combining the use of transcranial neurostimulation therapy with motion sensors of the vehicle and/or behavioral pattern mapping of the occupant. Where the transcranial neurostimulation system 105 is embedded into a portion of the vehicle, for example into a headrest of the vehicle, the occupant of the vehicle may not even perceive that an active therapy is in operation, effecting the treatment of motion sickness. Such a system and method may allow the occupant of the vehicle to carry out a task which would otherwise have been inhibited by the symptoms of motion sickness whilst travelling in the vehicle.

The arrangement shown in FIG. 3 illustrates one arrangement of the transcranial neurostimulation system 105, according to one embodiment. The headrest 107 comprises an adaptive support element 113 configured to conform to the profile of the head 101 of the occupant, for example when the occupant positions their head 101 near to or against the headrest 107. The headrest 107 comprises a material covering 115 over the outer surface of the adaptive support elements 113. The material covering 115 may be integral to the headrest 107 or may be supplied as an after-market component. The material covering 115 comprises a plurality of rows 117 of electrodes 109 stitched into the material 115. The rows 117 of electrodes 109 extend between a right-hand edge of the headrest and a bottom edge of the headrest 107 in one embodiment. However, the electrodes 109 may be arranged in any appropriate manner. The rows 117 of electrodes 109 comprise a plurality of rows 117a of anodes 109a and a plurality of rows 117b of cathodes 109b. In the arrangement shown in FIG. 3, the material 115 is provide with five rows 117a of anodes 109a and seven rows 117b of cathodes 109b. The bottom three rows 117a of anodes 109a overlap with the top three rows 117b of cathodes 109b. However, the anodes 109a and the cathodes 109b may have any appropriate arrangement relative to each other. In one arrangement, contact between the occupant's scalp and the electrodes 109 activates the transcranial neurostimulation system 105. Where the occupants head 101 contacts only a portion of the electrodes 109, for example, a lower portion 121 of the rows 117 of electrodes 109, the location of the contact may be determined by evaluating which of the rows 117a, 117b of anodes 109a and cathodes 109b have been electrically connected by virtue of the contact with the occupant's head 101. In this manner, the transcranial neurostimulation therapy is applied only in the region 121 of the headrest 107 that contacts the occupant's head 101.

It will be appreciated by those skilled in the art that although the disclosure has been described by way of example with reference to one or more examples, it is not limited to the disclosed examples and that alternative examples could be constructed without departing from the scope of the disclosure as defined by the appended claims.

It is to be understood that variations and modifications can be made on the aforementioned structure without departing from the concepts of the present invention, and further it is to be understood that such concepts are intended to be covered by the following claims unless these claims by their language expressly state otherwise.

What is claimed is:

1. A vehicle seat comprising:
a headrest comprising a material forming a covering; and
at least two electrodes formed into the headrest and electrically coupled to an electricity supply, wherein the at least two electrodes are configured to apply transcranial neurostimulation to a head of an occupant of the vehicle seat in response to the head contacting the headrest and completing an electric circuit between the at least two electrodes, and wherein the at least two electrodes comprise a conductive thread stitched and/or woven in the material.

2. A system, comprising:
a vehicle;
a vehicle seat coupled to the vehicle;
a headrest coupled to the vehicle seat and having a covering; and
a transcranial neurostimulation system coupled to the vehicle, comprising at least two electrodes formed into the headrest, wherein one of the at least two electrodes is coupled to an electricity supply and configured to apply an electric current from the electricity supply to a head of an occupant of the vehicle seat in response to the head contacting the headrest and completing an electrical circuit between the at least two electrodes, and wherein the at least two electrodes comprise conductive thread stitched and/or woven into a material of the covering of the headrest.

3. The system of claim 2, wherein the transcranial neurostimulation system further comprises:
at least one first sensor coupled to the vehicle and configured to determine a condition of the occupant of the vehicle seat.

4. The system of claim 3, wherein the at least one first sensor is configured to determine a direction the occupant of the vehicle seat is looking.

5. The system of claim 3, wherein the at least one first sensor is configured to determine at least one of a heart rate of the occupant of the vehicle seat and a blood pressure of the occupant.

6. The system of claim 3, wherein the at least one first sensor is configured to determine a temperature of the occupant of the vehicle seat.

7. The system of claim 3, wherein the at least one first sensor is configured to determine brain activity of the occupant of the vehicle seat.

8. The system of claim 3, wherein the at least one first sensor is configured to determine a respiration rate of the occupant of the vehicle seat.

9. The system of claim 3, wherein the at least one first sensor is configured to determine vocal activity of the occupant of the vehicle seat.

10. The system of claim 3, wherein the transcranial neurostimulation system further comprises:
at least one second sensor coupled to the vehicle and configured to determine an operational state of the vehicle.

11. The system of claim 10, wherein the at least one second sensor is configured to determine an acceleration of the vehicle.

12. The system of claim 2, further comprising:
a controller coupled to the vehicle and configured to adjust operation of the transcranial neurostimulation system depending on a condition of the occupant of the vehicle seat and/or an operational state of the vehicle.

13. The system of claim 2, wherein the transcranial neurostimulation system further comprises:
one or more actuators coupled to at least one of the vehicle seat, the headrest, and the covering and configured to position the at least two electrodes relative to the occupant of the vehicle seat.

14. The system of claim 2, wherein the covering of the headrest comprises a headrest cover configured to be removably attached to the headrest of the vehicle.

15. The system of claim 2, wherein the at least two electrodes comprise a plurality of rows of electrodes, and wherein the plurality of rows of electrodes comprises a plurality of rows of anodes and a plurality of rows of cathodes.

16. The system of claim 15, wherein at least one of the rows of anodes overlaps with at least one of the rows of cathodes.

17. The system of claim 2, wherein the at least two electrodes are arranged such that contact of the occupant's head against the headrest completes an electric circuit between at least one anode and at least one cathode.

18. A transcranial neurostimulation system for a vehicle, comprising:
an electricity supply;
at least two electrodes formed into a headrest of vehicle furniture, wherein one of the at least two electrodes is electrically coupled to the electricity supply and configured to apply an electric current from the electricity supply to a vehicle occupant's head in response to the head contacting the headrest and completing an electrical circuit between the at least two electrodes; and
a controller configured to control the application of electric current based on at least one of a vehicle occupant condition sensed by a first sensor and a vehicle operational state sensed by a second sensor, wherein the sensors and one of the at least two electrodes are electrically coupled to the controller.

19. The transcranial neurostimulation system for a vehicle of claim 18, wherein the vehicle furniture comprises a vehicle seat.

* * * * *